(12) United States Patent
Bae et al.

(10) Patent No.: US 8,377,684 B2
(45) Date of Patent: *Feb. 19, 2013

(54) TEST STRIP AND METHOD FOR MEASURING BLOOD CHOLESTEROL LEVEL USING THE SAME

(75) Inventors: Byeong-Woo Bae, Anyang (KR); Sung-Dong Lee, Anyang (KR); Byung-Hoon Kho, Seongnam (KR); Ji-Eon Ryu, Anyang (KR); Jin-Kyeong Kim, Gunpo (KR); Hyou-Arm Joung, Uiwang (KR)

(73) Assignee: Infopia Co., Ltd. (KR)

( * ) Notice: Subject to any disclaimer, the term of this patent is extended or adjusted under 35 U.S.C. 154(b) by 343 days.

This patent is subject to a terminal disclaimer.

(21) Appl. No.: 12/722,147

(22) Filed: Mar. 11, 2010

(65) Prior Publication Data

US 2010/0311091 A1 Dec. 9, 2010

(30) Foreign Application Priority Data

Jun. 4, 2009 (KR) ........................ 10-2009-0049648

(51) Int. Cl.
*C12M 1/34* (2006.01)
(52) U.S. Cl. .................. 435/287.1; 435/287.7
(58) Field of Classification Search ............... 435/287.1, 435/287.7
See application file for complete search history.

(56) References Cited

U.S. PATENT DOCUMENTS

| 5,135,716 | A | 8/1992 | Thakore |
| 5,786,164 | A | 7/1998 | Rittersdorf et al. |
| 7,049,130 | B2 * | 5/2006 | Carroll et al. ............... 435/287.2 |
| 7,087,397 | B2 | 8/2006 | Anaokar et al. |
| RE39,915 | E | 11/2007 | Rittersdorf et al. |
| 7,435,577 | B2 | 10/2008 | Lawrence et al. |
| 7,582,484 | B2 | 9/2009 | Jones et al. |
| 2003/0224471 | A1 | 12/2003 | Jones et al. |
| 2006/0063267 | A1 | 3/2006 | Lawrence et al. |

FOREIGN PATENT DOCUMENTS

| KR | 1020040013003 A | 2/2004 |
| KR | 1020060064807 A | 6/2006 |
| KR | 1020070092097 A | 9/2007 |

OTHER PUBLICATIONS

PCT/KR2010/002037 International Search Report Oct. 26, 2010.

* cited by examiner

*Primary Examiner* — Susan Hanley
*Assistant Examiner* — Bin Shen
(74) *Attorney, Agent, or Firm* — Cantor Colburn LLP

(57) ABSTRACT

Disclosed are a test strip and a method for measuring medical data. The test strip comprises an upper cover having one or more application holes; a lower support having one or more detected parts at positions corresponding to detecting units of the measuring apparatus; an erythrocyte and LDL cholesterol-filtering layer designed to filter off both of erythrocytes and LDL cholesterol from an applied blood sample by agglutinating erythrocytes and precipitating LDL cholesterol; and a reaction layer in which the blood sample free of erythrocytes and LDL cholesterol is reacted with an reagent, the filtering layer and the reaction layer being stacked between the lower support and the upper cover. Structured to filter off erythrocytes and low-density lipoprotein (LDL) cholesterol from a blood sample in a single layer, the test strip of the present invention can be made to be slim and allows a low volume of blood to be analyzed.

5 Claims, 3 Drawing Sheets

TEST STRIP AND METHOD FOR MEASURING BLOOD CHOLESTEROL LEVEL USING THE SAME

BACKGROUND OF THE INVENTION

1. Field of the Invention

The present invention relates, in general, to a test strip for measuring medical data and, more particularly, to a test strip for the analysis of medical data from blood. Also, the present invention relates to a method for measuring medical data using the test strip.

2. Description of the Related Art

The total cholesterol level in blood, plasma or serum is known as one type of medical data indicative of the risk of coronary arteriosclerosis. However, since recent clinical studies have shown a positive correlation between the level of low-density lipoprotein (LDL) cholesterol and the risk of coronary arteriosclerosis, LDL cholesterol levels are preferred as a medical indicator to total cholesterol levels.

LDL cholesterol levels can be measured using test strips in which suitable reactive agents are contained. Most of the measurement strips have a structure in which a plurality of pads containing reagents therein are stacked between an upper cover and a lower support. This stack structure is designed to flow a sample vertically. In this regard, the smoothness of the contact surfaces between an upper and a lower layer, together with the thickness of the pads, determines the flow rate and necessary amount of the blood. Particularly, in the case of dry biochemical strips comprising dry reagents, greater numbers of the pads or thicker pads give greater rise to measurement errors.

SUMMARY OF THE INVENTION

Accordingly, the present invention has been made keeping in mind the above problems occurring in the prior art, and an object of the present invention is to provide a test strip for measuring medical data accurately.

It is another object of the present invention to provide a method for measuring medical data using the test strip.

In accordance with an aspect thereof, the present invention provides a test strip for measuring medical data in association with a measuring apparatus, comprising: an upper cover having one or more application holes; a lower support having one or more detected parts at positions corresponding to detecting units of the measuring apparatus; an erythrocyte and low-density lipoprotein (LDL) cholesterol-filtering layer designed to filter off both of erythrocytes and low-density lipoprotein (LDL) cholesterol from an applied blood sample by agglutinating erythrocytes and precipitating LDL cholesterol; and a reaction layer in which the blood sample free of erythrocytes and low-density lipoprotein (LDL) cholesterol is reacted with an reagent, the filtering layer and the reaction layer being stacked between the lower support and the upper cover.

In accordance with another aspect thereof, the present invention provides a method for detecting cholesterol, comprising: filtering off erythrocytes and low-density lipoprotein (LDL) cholesterol from a blood sample; and reacting the blood sample free of erythrocytes and low-density lipoprotein (LDL) cholesterol with a reagent to generate medical data.

Structured to filter off erythrocytes and low-density lipoprotein (LDL) cholesterol from a blood sample in a single layer, the test strip of the present invention can be made to be slim and allows a low volume of blood to be analyzed.

BREIF DESCRIPTION OF THE DRAWINGS

The above and other objects, features and other advantages of the present invention will be more clearly understood from the following detailed description taken in conjunction with the accompanying drawings, in which.

DESCRIPTION OF THE PREFERRED EMBODIMENTS

Figure 1:
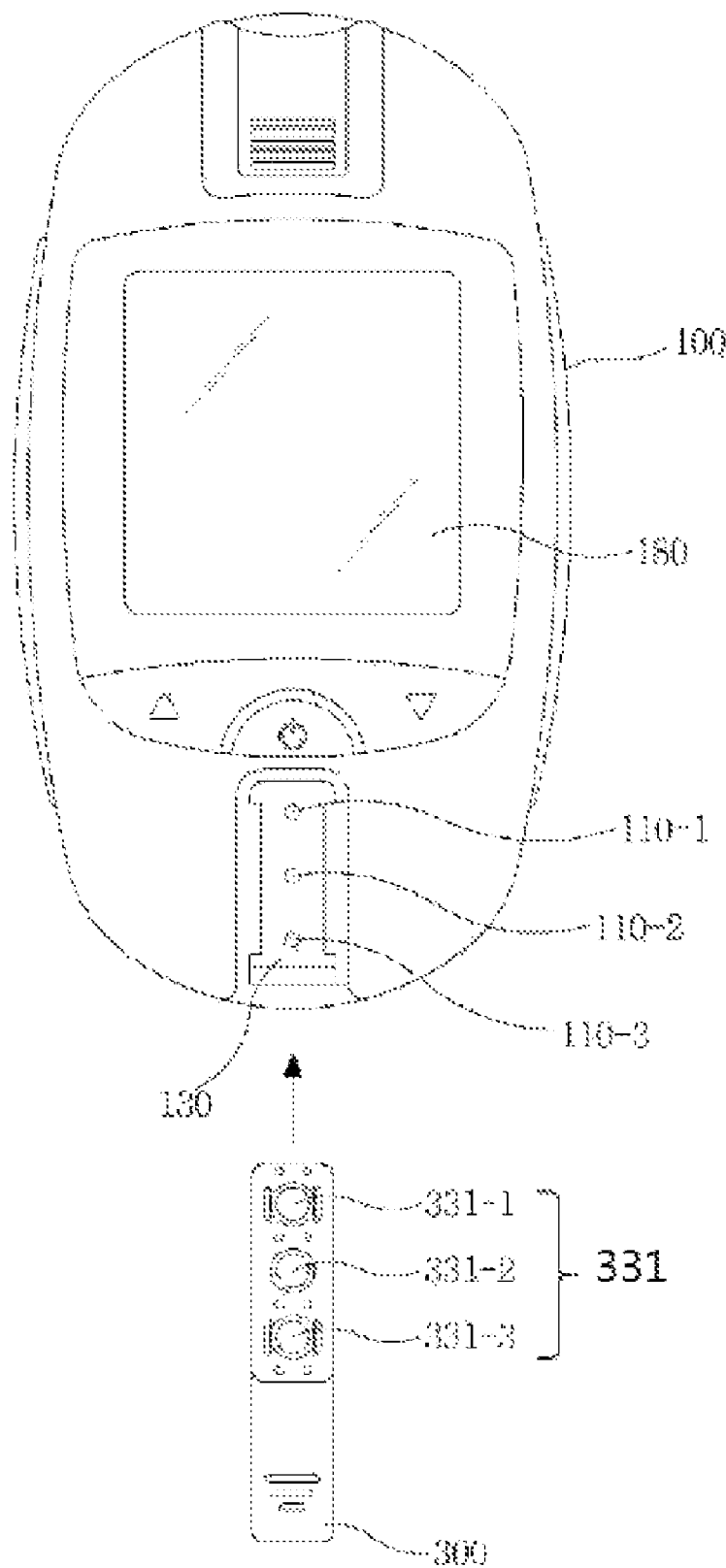
FIG. 1 is a schematic view showing an apparatus for measuring medical data and a test strip designed to be used in association therewith.

Reference now should be made to the drawings, in which the same reference numerals are used throughout the different drawings to designate the same or similar components.

FIG. 1 schematically shows an apparatus and a test strip for measuring medical data in accordance with an embodiment of the present invention. As seen in the schematic view of FIG. 1, the test strip 300 comprises a plurality of reaction regions 331 in which medical data, such as blood triglyceride and cholesterol levels, can be measured. The reaction regions 331 may differ in test target according to the positions thereof. For instance, the test strip of FIG. 1 has three reaction regions 331 adapted for measuring levels of total cholesterol, high-density lipoprotein (HDL) cholesterol and triglyceride, respectively, all of which are used to quantitatively analyze low-density lipoprotein cholesterol levels. The apparatus 100 for measuring medical data comprises a power button, an integrated strip adaptor 130, and a display 180. The strip adaptor 130 is provided with a plurality of spaced detecting units on the mid line thereof. The detecting units 110 are designed to correspond respectively to the reaction regions 331 of the test strip 300. Depending on test types, a part or all of the detecting units 110 are activated to detect reactions occurring in the reaction regions 331.

Figure 2:
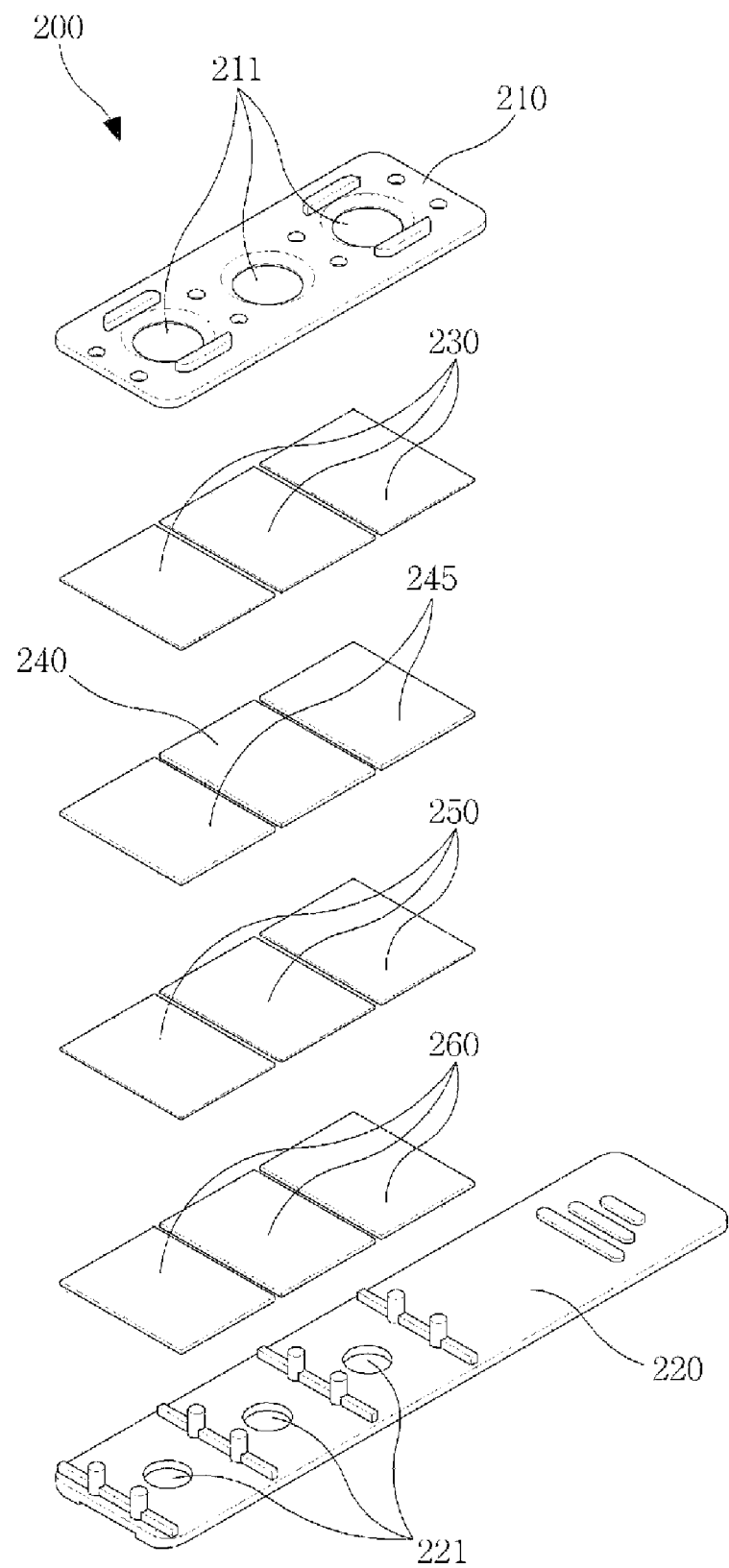
FIG. 2 is an exploded perspective view showing a test strip according to an embodiment of the present invention.

With reference to FIG. 2, a test strip 200 in accordance with an embodiment of the present invention is shown in an exploded perspective view. As seen in this exploded perspective view of FIG. 2, the test strip 200 comprises an upper cover 210 with a plurality of application holes 211 constructed therein, a middle structure separable into many stacked layers, and a lower support 220.

The upper cover 210 has one or more application holes 211 through which the user can load blood samples on the test strip and which may differ in measurement target from one to another. For example, the upper cover 210 has three application holes 211 to determine blood low-density lipoprotein cholesterol levels.

On the lower support 220, detected parts 221 are located at positions corresponding to the detecting units 110 of the strip adaptor 130 in the apparatus 100. The apparatus 100 determines medical data through the detected parts 221.

The middle structure comprises a blood-spreading layer 230, a blood-filtering layer divided into an erythrocyte and low-density lipoprotein (LDL) cholesterol-filtering zone 240 and erythrocyte-filtering zones 245, and a reaction layer 260. The erythrocyte and low-density lipoprotein (LDL) cholesterol-filtering zone 240 is located beneath the second application hole which targets high-density lipoprotein cholesterol (HDL) while the other regions account for the erythrocyte-filtering zones 245.

Constructed with a porous polyester mesh, a woven fabric such as a cotton fabric or gauze, the blood-spreading zone 230 mainly functions to spread the blood thereover quickly and uniformly.

The erythrocyte and low-density lipoprotein (LDL) cholesterol-filtering zone 240 is comprised of a glass fiber pad containing a hemagglutinating agent and an LDL cholesterol precipitating agent. The glass fiber pad ranges in diameter from 0.5 to 2 microns, and is 0.25~0.40 mm, and preferably 0.37 mm in length. Both the hemagglutinating agent and the precipitating agent are uniformly distributed in an impregnated or fixed form over the pad. The precipitating agent useful in the present invention may be lectin, a cation polymer and/or a saccharide. Examples of the lectin include PHA (phytohemagglutinin), concanavalin A, PWM (pokeweed mitogen) and wheat-germ agglutinin. Among the cationic polymers is poly(diallyldimethylammonium chloride). The saccharides useful in the present invention may be mono-, di- and/or polysaccharides, such as sorbitol, sugar, oligosaccharides, etc. Functioning to selectively precipitate LDL cholesterol in blood, the precipitating agent useful in the present invention may be selected from among sulfonated polysaccharides, heparin, phosphotungstic acid (PTA), dextran sulfate, and salts of Group II cations therewith. A detailed description will be given of the erythrocyte and LDL cholesterol-filtering zone 240, below.

The erythrocyte filtering zone is composed of a glass fiber pad containing a hemagglutinating agent. Among the hemagglutinating agents useful in the present invention, as mentioned above, is lectin, a cationic polymer or a saccharide. Examples of the lectin include PHA (phytohemagglutinin), concanavalin A, PWM (pokeweed mitogen) and wheat-germ agglutinin. Of the cationic polymer is representative poly (diallyldimethylammonium chloride). The saccharides useful in the present invention may be mono-, di- and/or polysaccharides. When the blood, after passing through the blood spreading layer 230, reaches the pad, the erythrocytes thereof are agglutinated by the hematogglutinating agent. The agglutinated erythrocytes cannot be transmitted to the reaction layer 260.

In order to obtain medical data, the reaction layer 260 is designed to react with the blood from which erythrocytes and LDL cholesterol are removed. The reaction layer contains a reagent which can react with the erythrocyte- and LDL cholesterol-free blood. The reagent may be impregnated or fixed into the pad. In a preferred embodiment of the present invention, high-density lipoprotein (HDL) cholesterol is quantitatively analyzed. In this case, HDL cholesterol is cleaved into free cholesterol and fatty acid by cholesterol esterase and the free cholesterol is reacted with oxygen in the presence of cholesterol oxidase to form hydrogen peroxide which undergoes a color reaction with a coloring reagent in the presence of peroxidase.

After being loaded to the test strip through the application holes 211, a blood sample spreads over the blood-spreading layer 230 and flows down to the erythrocyte and LDL cholesterol-filtering zone 240 and the erythrocyte-filtering zones 245. When reaching the erythrocyte and LDL cholesterol filtering zone 240, the erythrocytes of the blood sample agglutinate by reaction with an agglutinin such as sugar while LDL cholesterol is selectively precipitated by reaction with an LDL cholesterol-precipitating agent. Only the serum thus filtered flows down to the reaction layer 260. In the reaction layer, the blood free of erythrocytes and LDL cholesterol reacts with reagents for quantitatively analyzing cholesterol.

In an additional embodiment of the present invention, a hydrophilic material may be intercalated between the reaction layer 260 and the erythrocyte-filtering zone 245 or between the reaction layer 260 and the erythrocyte and LDL cholesterol-filtering zone 240. The term "hydrophilic material", as used herein, is intended to refer to a material which has an oxygen atom or a hydroxy radical at the terminal group or functional group thereof, such as polyvinylpyrrolidone (PVP), polyvinylalcohol (PVA) or polyethanol glycol (PEG), thereby allowing hydrophilic treatment. Located between the blood filtering layer and the reaction layer 260, the hydrophilic material 250 functions to prevent the penetration of the erythrocytes unfiltered by the blood filtering layer into the reaction layer 260 and to spread the filtered blood. In one preferred embodiment of the present invention, the hydrophilic material 250 may be in the form of a hydrophilized porous mesh. The mesh may have a pore size of from 1 to 500 μm and a thickness of 1 μm or less and may be composed of polyester. The porous mesh may be hydrophilized by reacting with a hydrophilic compound such as polyvinylpyrrolidone (PVP), polyvinylalcohol (PVA) or polyethylene glycol (PEG), or by introducing an oxygen atom or a hydroxy radical into the terminal group or functional group thereof.

Figure 3:
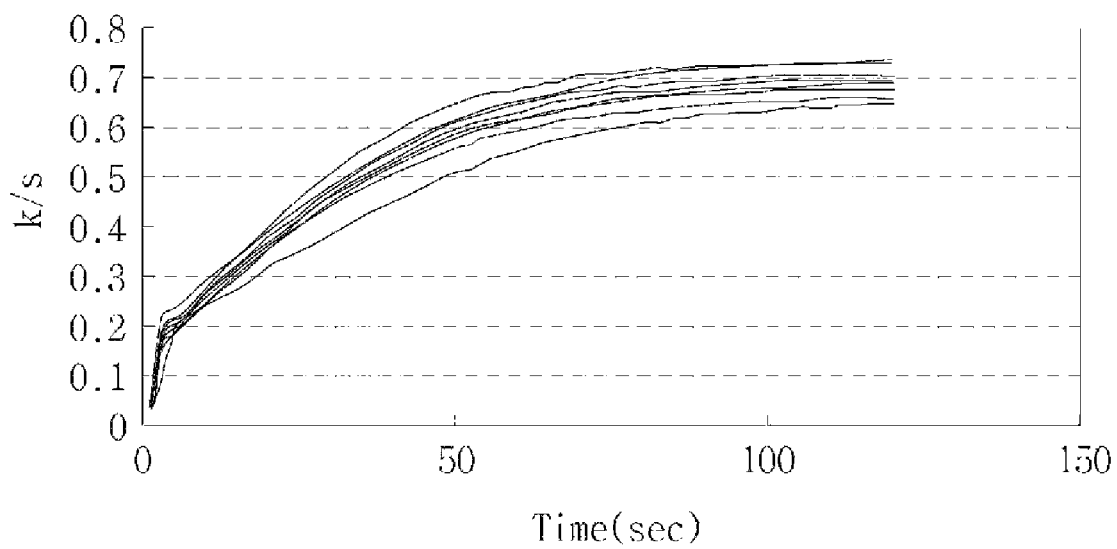
FIG. 3 is a graph showing the reflectance (k/s) obtained with a conventional test strip which is designed to separate erythrocytes and low-density lipoprotein (LDL) cholesterol in different layers.
Figure 4:
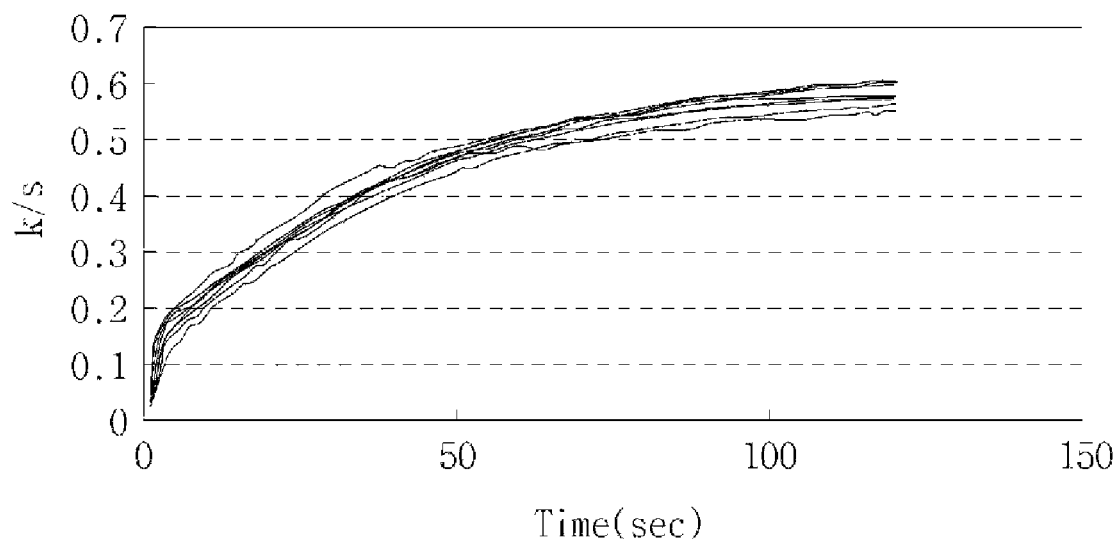
FIG. 4 is a graph showing the reflectance (k/s) obtained with a test strip of the present invention under the same condition.

FIGS. 3 and 4 are reflectance graphs obtained with a conventional test strip designed to separate erythrocyte and LDL cholesterol at different layers, and a test strip according to the present invention under the same condition, respectively.

In FIGS. 3 and 4, reflectance (k/s) is plotted five times against time, with the same blood loaded onto the strips. Both the plot patterns of FIGS. 3 and 4 are observed to converge on certain points, with narrower spaces given to the plots of FIG. 4. As for the coefficient of variation, it was found to be 5% among the plots of FIGS. 3 and 3% among the plots of FIG. 4. Because a lower coefficient of variation accounts for higher reproducibility with the same sample, the test strip of the present invention is better in reproducibility than is the conventional test strip. When a strip comprising a plurality of layers is used to separate blood into the components thereof, there is a measurement error due to a leakage in each layer and a deviation in junction between layers. Being structured to perform the separation of both erythrocytes and LDL cholesterol in one layer, the test strip of the present invention can greatly reduce the measurement error caused by the factors.

In the following examples, the erythrocyte and LDL cholesterol-filtering zone is described in detail.

A better understanding of the present invention may be obtained through the following examples which are set forth to illustrate, but are not to be construed as limiting the present invention.

EXAMPLE 1 trehaloze, phosphotungstic acid and magnesium sulfate were dissolved in amounts of 8, 4.5 and 0.5 wt %, respectively, in deionized water, followed by the adjustment of the solution to a pH of 6.5. In the solution were dissolved 0.1 wt % of polyvinylpyrrolidone K-30 and 0.5 wt % of dextran 70. The resulting solution was sprayed at a rate of 145 μL/sec over the a glass fiber pad which was then dried at 40° C. for 1 hr in an oven to prepare an erythrocyte and LDL cholesterol-filtering pad.

EXAMPLE 2

An erythrocyte and LDL cholesterol-filtering pad was prepared in the same manner as in Example 1, with the exception that trehalose was used in an amount of 8 wt %, 10 wt %, 12 wt %, or 15 wt %.

EXAMPLE 3

An erythrocyte and LDL cholesterol-filtering pad was prepared in the same manner as in Example 1, with the exception that polyvinylpyrrolidone K-30 was used in an amount of 0.1 wt %, 0.3 wt %, 0.5 wt %, 0.7 wt %, or 1 wt %.

EXAMPLE 4

An erythrocyte and LDL cholesterol-filtering pad was prepared in the same manner as in Example 1, with the exception that dextran 70 was used in an amount of 0.1 wt %, 0.3 wt %, 0.5 wt %, 0.7 wt %, or 1 wt %.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A test strip for measuring medical data in association with a measuring apparatus, comprising:
   an upper cover having one or more application holes for receiving a blood sample;
   a filtering layer having at least first filtering region and second filtering region, the first filtering region for filtering off erythrocytes from the blood sample by agglutinating erythrocytes and the second filtering region for filtering off both of erythrocytes and low-density lipoprotein (LDL) cholesterol from the blood sample by agglutinating erythrocytes and precipitating LDL cholesterol; and
   a reaction layer having first reaction region and second reaction region, wherein the filtered blood sample is reacted with an reagent in the first reaction region and the second reaction region,
   wherein the first filtering region and the second filtering region are disposed in a substantially same plane adjacent to each other, wherein the first reaction region is communicated with the first filtering region and the second reaction region is communicated with the second filtering region.

2. The test strip of claim 1, wherein the second filtering region includes a hematogglutinin selected from a group consisting of lectin, a cationic polymer, a saccharide and a combination thereof.

3. The test strip of claim 1, wherein the second filtering region includes phosphotungstic acid (PTA) as an LDL cholesterol-precipitating agent.

4. The test strip of claim 1, wherein the second filtering region includes dextran sulfate as a low-density lipoprotein (LDL) cholesterol-precipitating agent.

5. The test strip of claim 1, wherein the second filtering region includes as a low-density lipoprotein (LDL) cholesterol-precipitating agent, a combination of a divalent cation and one selected from a group consisting of phosphotungstic acid (PTA), dextran sulfate and a combination thereof.

* * * * *